United States Patent [19]
Wheeler

[11] Patent Number: 5,523,226
[45] Date of Patent: Jun. 4, 1996

[54] TRANSGENIC SWINE COMPOSITIONS AND METHODS

[75] Inventor: Matthew B. Wheeler, Tolono, Ill.

[73] Assignees: Biotechnology Research and Development Corp., Peoria; Board of Trustees of the University of Illinois, Urbana, both of Ill.

[21] Appl. No.: 63,095

[22] Filed: May 14, 1993

[51] Int. Cl.$^6$ ..................................................... C12N 5/00
[52] U.S. Cl. .............. 435/240.2; 435/7.23; 435/172.3; 435/240.21; 424/9.1; 935/70
[58] Field of Search ........................ 435/6, 7.23, 172.1, 435/172.3, 240.2, 240.21; 935/70; 800/2, DIG. 1

[56] References Cited

U.S. PATENT DOCUMENTS

| | | | |
|---|---|---|---|
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |

FOREIGN PATENT DOCUMENTS

| | | |
|---|---|---|
| 0169672 | 1/1986 | European Pat. Off. . |
| 2213831 | 8/1989 | United Kingdom . |
| WO90/03432 | 4/1990 | WIPO . |
| WO92/22646 | 12/1992 | WIPO . |

OTHER PUBLICATIONS

J. Nichols et al (1990) Development 110:134–1348.
E Notarianni et al Journal of Reproduction and Fertility v. supp. No. 41, 1990.
E Robertson et al (1986) Nature 323:445–448.
G R Martin (1980) Science 209:768–776.
J. A. Piedrahita et al., "Influence of Feeder Layer Type on the Efficiency of Isolation of Porcine Embryyo–Derived Cell Lines", *Theriogenology*, 34(5):865–877 (1990).
J. A. Piedrahita et al., "On the Isolation of Embryonic Stem Cells: Comparative Behavior of Murine, Porcine and Ovine Embryos", *Theriogenology*, 34(5):879–901 (1990).
E. J. Robertson, "Embryo–derived Stem Cell Lines", *Teratocarcinomas and Embryonic Stem Cells: a practical approach*, Chapter 4(4.4.2):92 (1987).
T. Doetschman et al., "Establishment of Hamster Blastocyst–Derived Embryonic Stem (ES) Cells", *Developmental Biology*, 127:224–227 (1988).
H. R. Axelrod, "Embryonic Stem Cell Lines Derived from Blastocysts by a Simplified Technique", *Developmental Biology*, 101:225–228 (1984).
A. Handyside et al., "Towards the Isolation of Embryonal Stem Cell Lines from the Sheep", *Developmental Biology*, 196:185–190 (1987).
G. R. Martin, "Isolation of a Pluripotent Cell Line from Early Mouse Embryos Cultured in Medium Conditioned by Teratocarcinoma Stem Cells", *Proc. Natl. Acad. Sci. USA*, 78(12):7634–7638 (1981).
R. M. Strojek et al., "A Method for Cultivating Morphologically Undifferentiated Embryonic Stem Cells from Porcine Blastocysts", *Theriogenology*, 33(4):901–913 (1990).
A. M. Wobus et al., "Characterization of a Pluripotent Stem Cell Line Derived from a Mouse Embryo", *Exp. Cell Res.*, 152:212–219 (1984).

(List continued on next page.)

*Primary Examiner*—Jacqueline M. Stone
*Assistant Examiner*—Bruce R. Campell
*Attorney, Agent, or Firm*—Alice O. Martin; Willian Brinks Hofer Gilson & Lione

[57] ABSTRACT

Transgenic swine, and compositions and methods for making and using same, are provided. Central to the invention are porcine (Sus scrofa) embryonic stem cell lines and methods for establishing them. Cells of such lines are transformed with exogenous genetic material of interest and then used to provide chimeric swine, which have germ cells comprising the exogenous genetic material. The chimeric swine are bred to provide transgenic swine. Transgenic swine of the invention can be used to provide human proteins or peptide hormones or can be used as xenograft donors.

5 Claims, 3 Drawing Sheets

OTHER PUBLICATIONS

K. R. Thomas et al., "Site-Directed Mutagenesis by Gene Targeting in Mouse Embryo-Derived Stem Cells", *Cell,* 51:503–512 (1987).

Hogan et al., "Isolation of Pluripotential Stem Cell Lines", *Cold Spring Harbor Laboratory—Manipulating the Mouse Embryo: A Laboratory Manual,* Section E: 205–218 (1986).

Clark et al. (1992) In: *Transgenic Animals,* Groveld et al., eds, Academic Press, p. 250.

Kolias et al. (1992) In: *Transgenic Animals,* Grosveld et al., Academic Press, p. 92.

Wurst et al. (1993) In: *Gene Targeting A Practical Approach,* Joyner, ed, IRL Press, p. 33.

FIG. IA
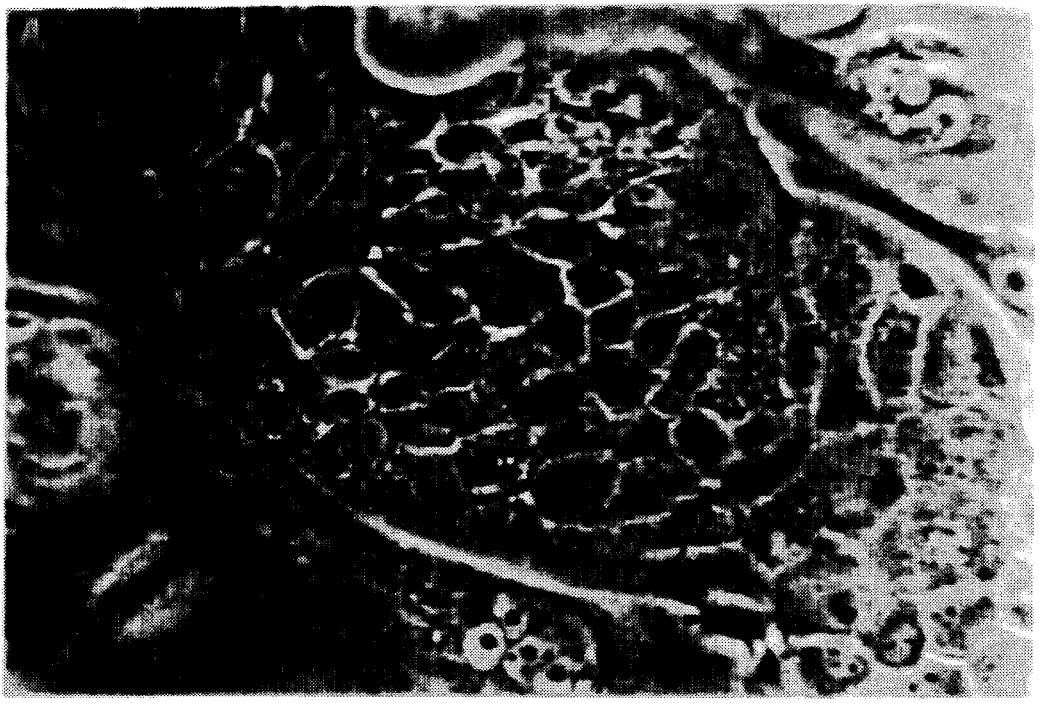
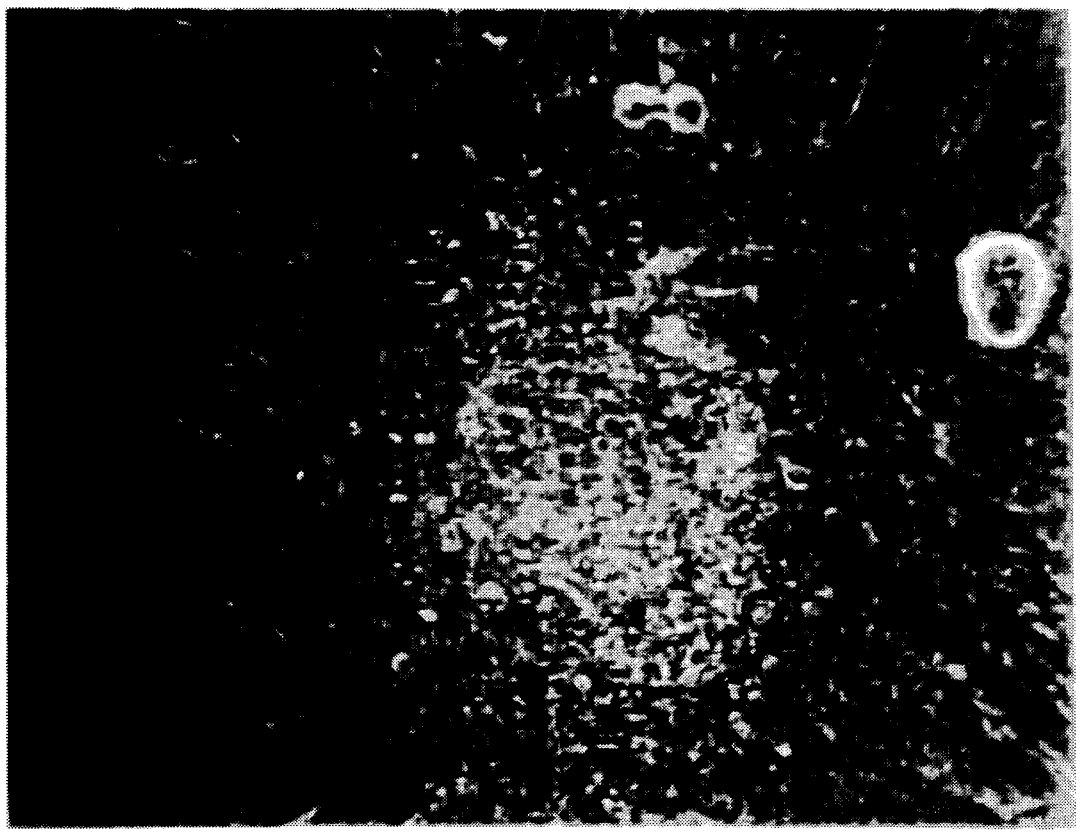
FIG. IB

FIG. IC
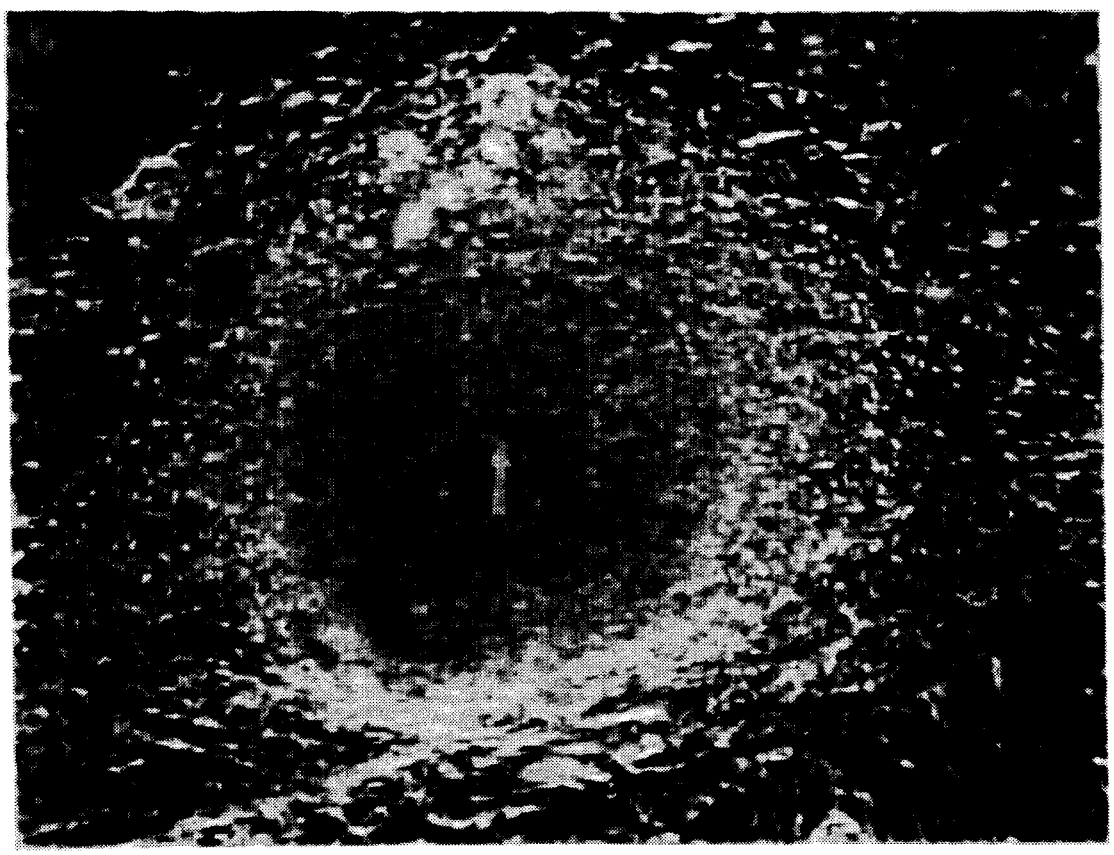
FIG. ID

TRANSGENIC SWINE COMPOSITIONS AND METHODS

BACKGROUND OF THE INVENTION

This invention relates to compositions and methods for making swine embryonic stem cells, chimeric swine from the stem cells, and transgenic swine from the chimeras.

Although transgenic animals have been produced by several different methods in several different species, methods to readily and reproducibly produce transgenic large mammals at reasonable costs are still lacking.

Methods to produce transgenic swine, for example, by microinjecting swine ova with genetic material, is very expensive. It costs between $25,000 to $250,000 to produce a single transgenic line. Another problem is that microinjection is a technically difficult procedure with an unacceptably low success rate. Furthermore, DNA transferred by microinjection is incorporated at random in the genome, usually in tandem linear arrays of multiple copies of the transgene. These limitations have resulted in animals being produced where 1) the transgene is not incorporated at all, 2) the transgene is incorporated but not expressed, 3) the transgene is incorporated but expressed transiently or aberrantly, and rarely 4) the transgene is incorporated and expressed normally. Also the incorporation of transgenes in the host genome may result in the disruption of an endogenous gene by a so-called insertional mutation, where some aspect of its development, growth or normal physiology is disrupted. Furthermore, this random insertion results in difficulties in controlling how the transgene will be regulated because flanking sequences upstream and downstream of the inserted transgenic DNA construct and which provide the control are randomly associated with the transgene.

One of the methods to generate transgenic animals, the use of transformed embryonic stem cells (ES-cells), has shown certain advantages over other methods when used to produce mouse chimeras, from which transgenic mice are derived. Once isolated, ES-cells may be grown in vitro for many generations producing unlimited numbers of identical cells capable of developing into fully formed adult chimeras. (Bradley et al., 1984)

A second major advantage of ES-cells is that they can be genetically manipulated in vitro. ES-cells may be transformed by introducing exogenous DNA into the cells via electroporation. Following transformation individual ES-cell clones may be screened in vitro for the incorporation of the exogenous DNA before being used to produce chimeric embryos (Thomas et al., 1987). ES-cell clones containing the transferred DNA can be selected and used for blastocyst injection. The ability to screen and select transformed ES-cells in vitro is one of the most important features for utilizing this strategy to produce transgenic animals.

When transformed ES-cells are used to make chimeric embryos, some of these cells may be incorporated into the gonads and participate in the formation of sperm and ova. Incorporation of the transgene into the gametes permits germ line transmission. Some of the offspring produced by chimeric individuals will be transgenic (Gossler et al., 1986, Robertson, 1987). A transgenic animal has the transgene in all of its cells, although not necessarily expressed. It is not the individual that results originally from the chimeric embryo that is transgenic, but offspring of that individual. This is an important distinction in as much as the chimeric individual can act as founder stock to produce many individuals that carry the desirable gene(s).

Early results have shown that use of chimeras is effective for producing transgenic mice. About 70% of expanded mouse blastocysts develop into live young with about 50% of the young born being chimeric (Bradley et al., 1984). Twenty percent of these chimeric young have germ cell chimerism. Utilizing this method it is not unreasonable to expect that chimerism in the germ line may be 20–30%.

The generation of transgenic animals depends on recombination of the exogenous DNA providing the transgene, with endogenous DNA. Although the majority of such recombinational events are non-homologous reactions, many cell types (including ES-cells) also possess the enzymatic machinery required for homologous recombination. The homology-dependent recombination between exogenous DNA and chromosomal DNA sequences is referred to as gene targeting, and it offers an additional dimension to transgenic technology. Gene targeting allows the transfer of genetic alterations/mutations created in vitro to precise sites within the host cellular genome. If the host cells are pluripotent ES-cells, such alterations can then be transferred to the germ line of a living organism.

ES cells have been used to produce transgenic lines of mice which through homologous recombination have directed gene insertion. This strategy of creating animals with specific genomic changes has immense potential in agriculture, and in furthering our understanding of the genetic control of mammalian development. However, the ES-cell method has not been successfully applied to production of larger transgenic mammals, for example, transgenic swine. A reason for the failure to extrapolate methods from mice to swine is the difference in developmental stages of the species. For example, the embryonic disc is not a solid mass in swine as in a 5-day old mouse. Other methods include embryonic infection with a recombinant molecule, for example, a retroviral vector with a transgene. Piedrahita et al. (1988, 1990) isolated potential swine stem cells, but was unable to maintain lines or demonstrate these cells' pluripotentiality.

Attempts to use embryonic carcinoma cells to produce chimeric mice, by introducing such cells into an embryo have had limited success. Martin (1981) reported growing mouse stem cells in media conditioned by the growth of teratocarcinoma cells. However, employing cancer cells in a growth environment is not likely to be palatable to the general public if such transgenic animals are to be used for products for human use, for example, food or organs for transplants. Chimeric pigs may be made in several ways, for example, by fusion of aggregates of embryonic cells such as morulas. Transgenic pigs are not derived from chimeras made in this fashion, because the fused cells maintain their genetic complements.

Notarianni et al. (1990) report methods to produce transgenic pigs by use of pluripotent stem cells but do not convincingly show that pluripotent embryonic stem cells were produced. Chimeric pigs were not reported as an intermediate step toward production of a transgenic pig. Pluripotent cells are defined as cells that are capable of being induced to develop into several different cell types. True totipotent embryonic cell types are those capable of being induced to develop into any cell type present in an entire animal.

The morphological description and figures illustrating some of the "selected" cells in the Evans patent application, International Publication No. WO90/03432, and publications from his group are more reminiscent of epithelial cells, than of embryonic stem cells from other organisms such as the mouse. Indeed, the authors state the "ES" cells from pigs are morphologically dissimilar from mouse ES-cells. Also, no biochemical tests were done to confirm that the selected cells were not differentiated. The only evidence of pluripotency was production of differentiated cells in culture.

Even if some embryonic stem cells were actually mixed into the "selected" cell population reported by Evans, use of these cell populations to produce chimeric pigs would be expected to be relatively inefficient because chance would dictate whether an embryonic stem cell would be included in the injected material. The probability of inclusion would be expected to be proportional to the percentage of embryonic stem cells in the mixed culture. The lack of a homogeneous culture would lead to inefficient and unpredictable results. Moreover, the method disclosed could not be described as "a method to produce embryonic stem cells," which implies homogeneity and reproducibility.

Evans teaches that a feeder cell layer is necessary for cell growth and teaches away from the use of conditioned medium or growth factors. A simpler culture method is desirable to reduce costs and improve throughput. A feeder layer and the use of conditioned media were also part of the methods of Piedrahita et al. (1988, 1990a and b and Gossler (1986). The Piedrahita et al. 1990a reference teaches away from conditioned medium.

Strojek (1990) describes methods and results similar to those of Evans. Trophoblastic cells and non-homogeneous cultures derived from swine embryos were disclosed.

Handyside (1987) attempted to produce chimeric sheep from embryonic stem cells, but was admittedly unsuccessful. Flake (1986) produced chimeras, but resorted to in utero transplant. Doetschman (1988) identified "embryonic stem cells" from hamsters by growing them on mouse embryonic fibroblast feeder layers. Pluripotency was determined by differentiation in suspension cultures. Ware (1988) reported embryo derived cells from "farm animals" growing on Buffalo Rat Liver BRL and mouse primary fetal fibroblasts.

Wall (1991) suggested using transgenic swine as factories to produce biological products, but did not teach how to accomplish this goal.

Improved methods for the production of transgenic pigs are needed. Transgenic animals are useful as models for diseases for the testing of pharmacological agents prior to clinical trials or the testing of therapeutic modalities. Another advantage is that more desirable qualities in farm animals may be produced by introducing desirable transgenes that can provide such desirable products. These desirable qualities include increased efficiency in feed utilization, improved meat quality, increased pest and disease resistance, and increased fertility.

Transgenic animals are an alternative "factory" for making useful proteins by recombinant genetic techniques. Large animals such as pigs, are potential factories for some products not obtainable from recombinant hosts that are microorganisms or small animals. An example of such products are organs which are transplantable into humans.

Embryonic stem cell transfer to produce transgenic pigs is an improvement over available methods. A reason that embryonic stem cell-mediated gene transfer has not been employed in domestic livestock is the lack of established, stable embryonic stem cell lines available from these species. The availability of such lines would provide feasible methods to produce transgenic animals.

Previous failures to identify and isolate ES cells in swine, may have been due in part to the expectation that such cells would be fast-growing and resemble those of the mouse. In some reports, malignant transformation was necessary to overcome the inherent quiescence of the embryonic disc. McWhir (1989).

Another problem in extrapolating from mice to ungulates, such as swine, is that exactly analogous stages do not exist in the embryos of mice and of ungulates owing to differences in their development. In ungulates, growth is generally slower, and the early embryonic ectoderm is present in a discoid arrangement and not as a solid mass as in the 5-day old mouse embryo.

In the present invention, limitations of the art are overcome by the production of stable, pluripotent swine embryonic stem cell cultures. These cell cultures are used to make chimeric pigs, an intermediate step in producing a transgenic pig. The invention differs in the stage of development of the host into which embryonic cells are introduced, in culture conditions, validation of potency, and production of a chimera.

SUMMARY OF THE INVENTION

The present invention overcomes problems and limitations in the art of producing transgenic swine by presenting a novel and reproducible method which includes use of stable, swine embryonic stem (ES) cell lines as host vehicles for gene transfer into swine. Transgenic animals possess an alteration in their DNA which has been stably incorporated into the genome as a result of intentional experimental intervention. Totipotent stem cells are preferred because these cells can be induced to develop into an entire embryo. Pluripotent stem cells are those shown to induce a host structure from any one of the three germ cell layers: endoderm, ectoderm, mesoderm. Totipotent stem cells are also pluripotent, but the converse is not necessarily true.

In the present method, a cell from an embryonic stem cell line is introduced into a host embryo to create a chimeric pig, a certain percentage of which pigs so formed are germ cell chimeras. In mammals, germ cells segregate from somatic cells at the early primitive streak stage. Transformation of a cell occurring after that time results either in a transformed germ or a transformed somatic cell. These chimeras give rise to transgenic lines by breeding the chimeric animals and by selecting offspring of the breeding that exhibit transgenic expression. These are sometimes referred to as "germline transgenics." Alternatively, nuclei from the ES cell line are transferred into a cell from which an embryo develops.

Among the advantages of using embryonic stem cells to produce transgenic swine, are that efficiency is improved, and that transformed ES-cells can be used as the progenitors of clonal lines (descendent lines having the same genotype as the single parental cell, barring mutation). These clonal lines are manipulated to alter their genetic complement. Large numbers of the altered cells may be replicated in vitro so that replicate animals may be produced.

A significant advantage of the present method is the control and reproducibility of genetic manipulation. Introduction of transgenes to specific chromosomal locations is referred to as "gene targeting" because it allows the reproducible incorporation of a nucleotide sequence into a specific location of the host genome. Many cell types, including the embryonic stem cells of the present invention, possess the enzymatic machinery necessary to direct homologous recombination.

In an illustrative embodiment, a genetic mutation created in vitro is incorporated into a specific site of a host cell genome. If the transformed host cell is a pluripotent or totipotent embryonic stem cell, and said stem cell is incorporated into a chimeric pig, a transgenic animal is produced with a specific genetic change in a specific location of the host genome. For purposes of the present invention, a pluripotent stem cell is defined as an undifferentiated cell which is capable of being induced to develop into more than one differentiated cell type; a totipotent stem cell is defined as an undifferentiated cell which is capable of being induced to develop into all cell types. The requirement for proceeding from a chimeric to a transgenic pig, is that a gamete is a descendant of an embryonic stem cell. Existence of stable cell cultures allows development of a clone of ES cells with the same altered genetic complement, therefore, the opportunity arises to make replica swine with the same genetic complement.

The strategy of creating animals with specific genetic changes has immense potential use in agriculture. This use includes producing plants and animals with new, improved genomes. These improvements may be in the plant or animal itself, such as reduced spoilage or better taste, or may be in new uses for the transformed plant or animal, for example as a factory to produce pharmaceuticals, or as a production line for organs used in human transplants. The methods and compositions of the present invention bring these strategies into actuality.

The individual cell lines are readily screened to detect homologous or non-homologous recombination of exogenous DNA into chromosomal DNA. Using cell lines produced by the methods of the present invention, transgenic pigs with a transgene in a specific chromosomal location are produced. Stable, genetically altered lines of transgenic pigs are readily produced by introducing specific genes, at specific locations. Homologous recombination is used to integrate single genes in specific locations, avoiding the introduction of multiple copies of genes, and unpredictable numbers and locations of copies, which have caused problems in previous methods to produce transgenic animals. Insertion of single copies of genes circumvents some of the problems arising from integration of multiple copies as observed when growth hormone genes were introduced into transgenic pigs produced by other methods.

Versatility in the kinds of genetic manipulation possible in embryonic stem cell cultures, reproducibility of the methods to make such cultures, and predictability of results of genetic manipulation are other advantageous aspects of the present invention.

A method for producing a chimeric swine includes an initial step of introducing a swine embryonic stem (ES) cell which preferably is totipotent and that has a first genetic complement, into a host embryo which has a second swine genetic complement, to make a chimeric swine embryo.

A nucleotide segment of the first genetic complement is obtained by isolation from genomic DNA, preparation from cDNA, by direct synthesis, by recombinant techniques, or a combination thereof. Appropriate regulatory sequences are included.

In an illustrative embodiment, production of transgenic swine is achieved by placing the chimeric swine embryo into an environment suitable for the completion of development to form a chimeric swine, and developing the chimeric swine embryo to sexual maturity. The chimeric swine may be bred to produce an offspring.

It is preferable to determine whether the offspring is a transgenic pig by detecting the first genetic complement in the offspring, either by detecting its expression product, or a specific nucleotide sequence (the transgene).

Preferably the cell is introduced into an embryo at a pre-blastocyst stage. This can be at any stage from a one cell embryo to a blastocyst. The morula is particularly preferred.

Swine are generally of the genus and species Sus scrofa. In an illustrative embodiment, the chimera comprises embryonic stem cells from a first breed of swine, for example, the Meishan line and a morula from a second breed of swine, for example, the Duroc line.

The transforming first genetic complement, for example, an isolated nucleotide sequence, is selected according to a particular goal or goals of producing a transgenic swine. Limitations on transformation are those limitations generally known to those of skill in the art. The first complement may be different from the second. The first genetic complement could be a nucleotide sequence which is foreign to the species of the host (recipient), or it could be natural to the host species. In the latter case, the nucleotide sequence could be altered from that naturally present in the host.

Exogenous nucleotide segments which are desirable to use as a first genetic complement which is incorporated into chimeras, and subsequently transgenic swine, include genes encoding:

1) blood clotting factors such as Factor VIII and IX;
2) TNFα which is useful for inhibition of adipocytes;
3) growth factors such as
   a) EGF, which is useful for recovery of gastrointestinal linings disrupted after neonatal diarrhea;
   b) NGF, the neural growth factor;
4) iron-binding lactoferrin;
5) hemoglobin for artificial blood or treatment of anemia;
6) hormones such as insulin, FSHβ, GH, LHβ, PMSG; and
7) genes designated as
   a) SLA or MHC which are associated with disease resistance;
   b) cytokine genes;
   c) complement genes.

Angiogenic factors, pharmaceutical or diagnostic proteins, and antibodies are other useful products that may be manufactured by transgenic swine, for example, in their milk.

An initial step in the method is to establish a stable, undifferentiated embryonic stem (ES) cell line. For purposes of the present invention, stable means maintaining essentially similar cell types and growth parameters, through serial subcultures, under the same environmental conditions, and maintaining a stable chromosome complement of about 38. Undifferentiated in this context means not showing morphological or biochemical evidence of differentiation. An embryonic stem cell is an undifferentiated cell which is capable of differentiating into embryonic structures. An embryonic stem cell line is derived from a culture of embryonic stem cells. Using methods disclosed herein, ES-cells were developed from Meishan, Yorkshire and Duroc swine. Efficiency of producing ES-cells is somewhat affected by strain or breed of donor. Other suitable breeds or types include the NIH mini-pigs, feral pigs, SLA haplotyped swine, and the like.

A preliminary step in isolating swine embryonic stem cells is to collect swine embryos. Female pigs are checked for estrus, preferably twice daily. Donor sows for the ES-cells are inseminated at the time of the female pig's estrus. Embryos are then collected on days 5.5–7.5 post estrus if expanded blastocysts are desired, on days 1.5–5.5 post estrus if the pre-blastocyst stage is sought, or on days 7.5–10.0 post estrus if hatched blastocysts are sought.

Embryo cultures are then initiated using suitable media, culture dishes, temperature, and other conditions. In an illustrative embodiment, embryos are grown on or with feeder layers of cells. Differentiated cells will not attach to the feeder layer, or attach poorly. After about 24–48 hours in culture, expanded blastocysts generally hatch from the zona pellucida and attach to the culture dish. Alternatively, hatched blastocysts attach to the culture dish after about 24–48 hours in cultures (range 1–10 days).

Initial attachment of the hatched porcine blastocyst to the feeder layer or culture vessel (in conditioned stem cell media (CSCM)) is different from the mouse blastocyst. In the mouse, the hatched blastocyst (HB) plates down and attaches with the inner cell mass (ICM) growing up like a hilus or polyp. The trophoblast cells grow outward from the ICM, leaving a clear zone between the ICM and the trophoblast cells. This configuration allows for easy plucking of the ICM, essentially free of trophoblast cell contamination. The isolated ICM can then be put in trypsin to dissociate the cells for further subculture.

On the other hand, the pig HB attaches and plates down in a large clump and then begins to spread out as if it were melting. Consequently, the ICM is associated with trophoblast cells and its configuration resembles a fried egg in appearance. This phenomenon makes it difficult initially (first several days, 1–5) to pluck the ICM alone, and as a result, depending on the plated configuration of the individual embryo, the ICM may be plucked or the entire plated embryo may be trypsinized to dissociate the cells. After discrete multilayered clumps or colonies of ES cells are visible then plucking is done to isolate these cells from contaminating trophoblast and/or other differentiated cell types. This results in purification of cells with the proper ES morphology.

Embryonic stem cells are isolated from the attached embryos and maintained in cultures. The inner cell mass (ICM) of the cultured embryo is evident during the first 1–14 days of culture. After the ICM emerges, it is dislodged from the culture dish, and its cells are disaggregated, generally by a combination of proteolytic enzymes and mechanical agitation.

The disaggregated cells are cultured until nests of round cells appear, generally after 7–8 days (range ~2–21 days) in culture. Conditioned stem cell medium in the absence of a feeder layer is preferred for this growth stage.

Serial subculture is then performed at intervals that are a function of growth rate. In an illustrative embodiment, subculture intervals are from 2–14 days (range 1–21 days). As with embryo cultures, feeder cell layers may be used to support growth. Subculturing the culture is continued until a stable culture with morphological features and growth parameters characteristic of an embryonic stem cell culture is established.

As a preliminary scan for pluripotency of the ES cell lines, undifferentiated morphology is sought using the light microscope. Morphologically ES-cells are small (about 8–15 microns in diameter) and rounded, and possess large dark nuclei which contain one or more prominent nucleoli. The cytoplasmic to nuclear ratio is about 15:85, and the growth parameters comprise a doubling time of approximately 18–36 hours and multilayered rather than monolayered growth. A preferred method for identifying an embryonic swine stem cell suitable for incorporation into a host swine embryo, include the following steps:

(a) introducing a first embryonic stem cell from a culture into an immunodeficient mammal;

(b) allowing a tumor to form in the mammal from the embryonic stem cell;

(c) initiating a culture from a cell of the tumor; and (d) selecting a second embryonic stem cell from the tumor culture.

Lack of differentiation may also be determined by absence of cytoskeletal structural proteins such as cytokeratin 18 and vimentin, which are only expressed in differentiated cell types. Conversely, ability of the cells to differentiate after induction, is detected by loss of typical undifferentiated ES-cell morphology and positive fluorescent antibody staining with anti-cytokeratin 18 and anti-vimentin.

Established embryonic stem cells grow rapidly, dividing about every 18–36 hours. To protect against spontaneous, unwanted differentiation, cells are generally kept at a high density. Changing media and subculturing are used to maintain healthy, cultures of the appropriate density, generally about $1-2 \times 10^6$ cells/100 mm dish which contains about 10–12 ml of medium. The modal chromosomal count, that is, the number of chromosomes characteristic of the euploid pig genome, is 38.

Transformation of an embryonic stem cell in vitro with a first genetic complement which includes a nucleotide sequence is accomplished by any of the methods known to those of skill in the art. Examples of said methods include electroporation (calcium phosphate), use of a transforming vector (retrovirus), and lipofection, microinjection, or other means.

After selecting a suitable embryonic cell, which may be transformed, it is introduced into a cell or cells of a pig host embryo at the desired stage, generally the morula or blastocyst stage. The morula stage is preferred because the cells are fewer and less differentiated than cells of the blastocyst, consequently, a higher percentage of chimerism in more diverse cell types, is expected. Other stages are also suitable, for example, the one cell, two cell or 8 cell stage. The embryos are then immediately transferred into suitably prepared recipient gilts, or held in culture for up to about 10 days. (Polge, 1982; Webel et al., 1970).

Any method for introducing the cell into the host embryo is suitable, including microinjection. If the introduction is successful, a chimeric pig is produced. The chimerism is detected by an assay for the gene that was introduced via the transformed embryonic stem cell. For example, a skin pigment gene not present in the host blastocyst genome, may be detected as spots in the pig.

A pig that is produced from the embryo into which the transformed embryonic cell has been introduced is a presumed chimeric pig. Of course, not all pigs so produced are actually chimeric due to technical variation and chance. However, the success rate per embryo is higher (~30%, range 25–100%) than reported by others attempting to produce transgenic pigs using microinjection.

The presumed chimeric pigs are then bred to produce offspring. Some of the chimeric pigs used as parents have a transformed gamete. If a transformed gamete is used in fertilization, the resulting offspring is a transgenic pig, because all of its cells are descended from the zygote formed by the transformed gamete, therefore, all of the offspring's cells are expected to be transgenic. Of course, not all the offspring of chimeric pigs are transgenic, because not all chimeric pigs have transformed gametes, or have all of their gametes transformed.

To produce a transgenic pig, the genetic complement, for example, an isolated nucleotide sequence initially used to transform an embryonic stem cell of the present invention, must be incorporated into the genome of the host. If the transforming nucleotide sequence consists of exogenous DNA, which is generally the case, the exogenous DNA must become incorporated into the endogenous DNA of the host. Incorporation is generally accomplished by non-homologous recombination. However, homologous recombination may also be the means for achieving DNA incorporation. Homologous recombination is defined herein as recombination between related or identical DNA sequences; non-homologous recombination as recombination between unrelated DNA sequences. Caution is warranted at this stage because a foreign gene may disrupt normal development.

Transgenic swine with altered tissue or milk proteins or compounds produced as a result of protein production, include pharmaceutical, therapeutic, biomedical, processing, manufacturing or compositional proteins such as the following:

1) blood proteins (clotting factors VIII and IX, complement factors or components, hemaglobins or other blood proteins and the like;
2) hormones (insulin, growth hormone, thyroid hormone, catecholamines gonadotrophins, PMSG, trophic hormones, prolactin, oxytocin, dopamine and the like;
3) growth factors, i.e., EGF, PDGF, NGF, IGF's and the like;
4) cytokines, i.e., interleukins, CSF, GMCSF, TNF, TGFα and β and the like;
5) enzymes (tissue plasminogen activator, streptokinase, cholesterol biosynthetic or degradative, digestive, steroidogenic, kinases, phophodisterases, methylases, demethylases, dehydrogenases, cellulases, proteases, glycosolases, lipases, phospholipases, aromatase, cytochromes, adenylate or guanylate cyclases and the like);
6) hormone or other receptors (LDL, HDL, steroid, protein, peptide, lipid or prostaglandin and the like);
7) binding proteins (steroid binding proteins, growth hormone or growth factor binding proteins and the like);
8) immune system proteins (antibodies, SLA or MHC genes);
9) antigens (bacterial, parasitic, viral, allergens and the like);
10) translation or transcription factors, oncoproteins or proto-oncoproteins, milk proteins (caseins, lactalbumins, whey and the like); and
11) muscle proteins (myosin, tropomyosin and the like).

ES cells introduced into SCID (or other immune deficient or immuno-comprimised mice) mice produce tumors. These may be teratomas or teratocarcinomas, comprised of a number of fully differentiated tissues (including: muscle, bone, fat, cartilage, skin, epithelia, nervous, glandular, hemapoetic, secretory and the like). Each line of transgene carrying ES cells can be injected into SCID (or other immune deficient or immuno-comprimised mice) and the tumors harvested. In situ hybridization, immunocytochemistry, solution hybridization, Northern, Southern or Western analysis or the like can then be performed to determine which tissue types express the transgene. This methodology could allow for the rejection of transformed ES lines in which proper expression of the transgene did not occur. Further, this method could be a short cut to chimera or transgenic animal production in gene regulation studies.

This aspect of the present invention may be extrapolated to other species (cattle and buffalos, sheep, goats, horses) as well as swine as a system to screen embryonic cells for transgene expression prior to production of transgenic animals.

BRIEF DESCRIPTION OF DRAWINGS

FIGS. 1A–1D are a comparison of morphological characteristics of development of cells designated "stem cells" by Evans (top panel) and the "embryonic stem cells of the present invention" (bottom panel).

(FIG. 1A) nest of undifferentiated cells in an established cell line at 250× magnification (FIG. 5A, Evans patent, photo is same as FIG. 3A from Notarianni et al., 1990, where this photo was taken from, i.e., FIG. 5A patent=FIG. 3A Notarianni et al., 1990);

(FIG. 1B) cluster nest of undifferentiated "embryonic stem cells" from an established cell line of the present invention at 200× magnification;

(FIG. 1C) monolayer growth of Evans undifferentiated cells (FIG. 5B, Evans); versus (FIG. 1D) multilayered growth of the "embryonic stem cells" from an established cell line of the present invention at 200× magnification.

DETAILED DESCRIPTION OF THE PREFERRED EMBODIMENTS

Figure 2:
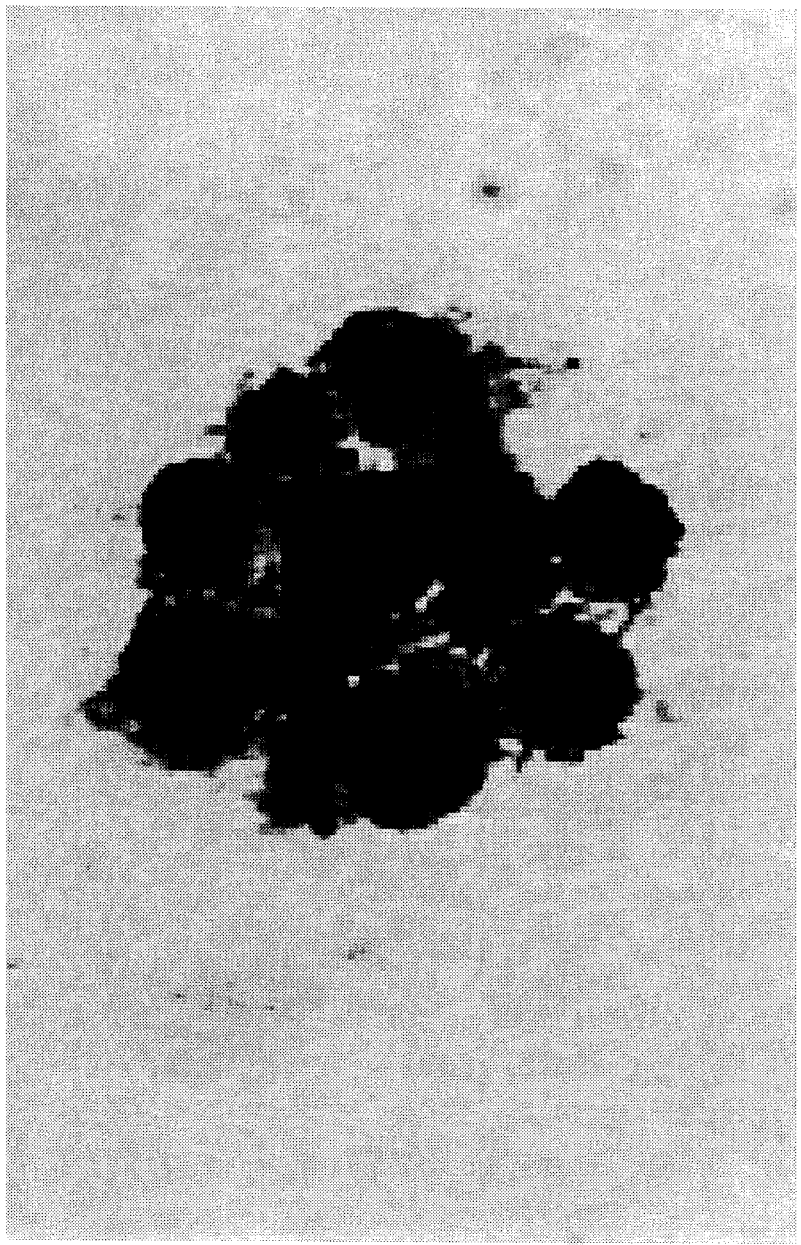
FIG. 2 ES cells of the present invention stained wth Giemsa at 400×; cells are dispersed and fixed on slides.

The following protocols and procedures are embodiments of various aspects of the invention. Formulation of various media, solutions and the like, are found in the Materials and Methods section.

1. Purification of Undifferentiated Embryonic Stem (ES) Cell Lines

Step 1:

Isolated, individual porcine embryos allowed to developed either in vivo or in vitro and allowed to escape from the zona pellucida either by natural hatching, mechanical or chemical removal were initially cultured on either (1) mitomycin C- inactivated mouse embryonic fibroblast (STO) monolayer or other cell layer with ES culture medium (SCM) which consisted of Dulbecco's Modified Eagle's Medium with only Fetal Calf Serum (20%), β-mercaptoethanol, antibiotics, nucleosides and non-essential amino acids, or (2) in conditioned stem cell medium (CSCM) which consisted of ~40% Dulbecco's Modified Eagle's Medium (DMEM) and ~60% Buffalo Rat liver cell conditioned medium (BRL-CM) containing a total of approximately 20% fetal calf serum (FCS), β-mercaptoethanol, antibiotics, nucleosides and non-essential amino acids (Smith and Hooper, 1987).

Step 2:

After about 4–21 days the colonies are (1) plucked, that is, removed selectively from a dish, or (2) the whole dish may be dispersed with trypsin and plated onto plates containing only conditioned medium (treatment 1), or plated onto STO feeder layers (treatment 2), as disclosed herein. PROTOCOL: ES cell colonies are dislodged from the underlying cells and washed through two changes of calcium/magnesium-free PBS. Alternatively, the entire dish of cells may be trypsinized. The colonies are then transferred to drops of trypsin solution (0.25% trypsin, 0.4% EDTA in Ca++, Mg++-free phosphate buffered saline, PBS; 1.0% NaCl, 0.025% KCl, 0.025% $KH_2PO_4$ and 0.114% $Na_2HPO_4$, pH 7.2) and incubated for 1–5 min at 37°–39° C. The cells are disaggregated by vigorous pipetting with a fine bore Pasteur pipette. The colonies are placed in 1 ml of conditioned stem cell medium (CSCM) to neutralize the trypsin. CSCM is comprised of ~40% Dulbecco's Modified Eagle's Medium (DMEM) and ~60% Buffalo Rat liver cell conditioned medium (BRL-CM) containing a total of approximately 20% fetal calf serum (FCS), β-mercaptoethanol, antibiotics, nucleosides and non-essential amino acids (Smith and Hooper, 1987). ES cells in both treatments are allowed to grow in the culture.

Step 3:

After an additional 2–21 days the colonies are either plucked (treatment 1) or the whole dish (treatment 2) is placed onto plates containing only conditioned medium. ES cells in both treatments are allowed to grow in culture. Feeder layers may also be used to support growth, but is not preferred. Either SCM or CSCM may be used in the presence of a feeder layer. (see Table 5)

PROTOCOL: as above in step 2

Step 4:

After an additional 2–21 days the colonies are either plucked (treatment 1) or the whole dish (treatment 2) is placed onto plates containing only conditioned medium. ES cells in both treatments are allowed to grow in culture.

PROTOCOL: as above in step 2

Step 5:

After an additional 2–21 days if there are sufficient cell numbers, $5-10 \times 10^6$ cells, then part of the cells are subcultured and part are frozen to act as a back-up stock of these stem cell colonies.

Step 6:

The cells that were cultured in only CSCM (or with feeder cells through step 2) are passed every 2–4 days in only CSCM. Until ES cell lines with consistent morphology, size 8–15μ, with a nuclear to cytoplasmic ratio of ~85:15, and growth characteristics (doubling time 18–36 h) are established. This entire process (Steps 1–6) may take from 5–21 weeks to isolate a single ES cell line. There lines are then used for production of chimeras and/or nuclear transfer. The next step is required to identify whether the proper cells have been isolated at this point of the procedure.

Step 7:

This step in the isolation procedure involves injection of the ES-cells underneath the tunica albuginea of the testis of immune system compromised mice (SCID, irradiated nude) to produce teratocarcinomas. The mice are examined for the presence of tumors daily. When palpable tumors are observed the mouse is euthanized and the tumor harvested. Undifferentiated ES cells are recovered from the tumor and re-introduced into in vitro culture. ES cell lines with appropriate morphology, size 8–15μ, with a nuclear to cytoplasmic ratio of ~85:15, and growth characteristics (doubling time of 18–36 h) are reestablished in culture and selected as in Step 6. These lines are used for production of chimeras and/or nuclear transfer.

NOTE: This step may occur at any point where ES cells of proper morphology are observed.

Step 8:

Periodically it is necessary to pluck colonies as outlined above and re-isolate the ES cells with consistent morphology, size 8–15μ, with a nuclear to cytoplasmic ratio of ~85:15, and growth characteristics (doubling time of 18–36 h).

NOTE: Maintenance of these isolated, purified undifferentiated ES cell lines is required to insure the proper cell type for generation of chimeras and for nuclear transfer. Some differentiation occurs spontaneously during in vitro culture and as a result of the freezing process. These differentiated cells do not subculture well, but occasionally it is necessary to re-purify the ES cells from the differentiated cells.

Step 9:

To obtain enriched populations of ES cells (size 8–15μ with a nuclear to cytoplasmic ratio of ~85:15, and doubling time of 18–36 h) for chimera production or nuclear transfer, ES cell colonies were dislodged from the underlying cells and washed through two changes of calcium/magnesium-free PBS. The colonies were then transferred to 50 μl drops of trypsin solution and incubated for 1–5 min at 37°–39° C. The colonies were placed in 1 ml of conditioned stem cell medium (CSCM) to neutralize the trypsin. The cells were disaggregated by vigorous pipetting with a fine bore Pasteur pipette.

Purification of swine ES-cells may also be performed by centrifugal elutriation, flow cytometry, unit gravity sedimentation, differential centrifugation, cell separation, immuno-surgery to preferentially kill mouse cells or differentiated swine cells, plucking of colonies or individual cells, differential or immuno-staining, production of chimeric embryos and re-isolation of inner cell mass and stem cells, affinity chromatography of ES vs. other swine cell types or mouse cells, mobility in electric fields, and the like.

TREATMENT 1:

ES cell Colonies are dislodged from the underlying cells and washed through two changes of calcium/magnesium-free PBS. The colonies are then transferred to 50 μl drops of trypsin solution (0.25% trypsin, 0.4% EDTA in Ca++, Mg++ -free phosphate buffered saline, PBS; 1.0% NaCl, 0.025% KCl, 0.02.5% $KH_2PO_4$ and 0.114% $Na_2HPO4$, pH 7.2) and incubated for 1–5 min at 37°–39° C. The cells are disaggregated by vigorous pipetting with a fine bore Pasteur pipette. The colonies are placed in 1 ml of conditioned stem cell medium (CSCM) to neutralize the trypsin. CSCM is comprised of ~40% Dulbecco's Modified Eagle's Medium (DMEM) and ~60% Buffalo Rat Liver cell conditioned medium (BRL-CM) containing a total of ~20% fetal calf serum (FCS), β-mercaptoethanol, antibiotics, nucleosides and non-essential amino acids (Smith and Hooper, 1987). The cells are pelleted by gentle centrifugation and either; 1) left at room temperature overnight followed by subculture onto new petri plates with CSCM or 2) immediately subcultured onto new petri plates with CSCM.

TREATMENT 2:

Plates containing ES cell colonies and underlying cells are washed through two changes of calcium/magnesium-free PBS. The plates had 1–5 ml of trypsin solution (0.25% trypsin, 0.4% EDTA in Ca++, Mg++-free phosphate buffered saline, PBS; 1.0% NaCl, 0.025% KCl, 0.025% $KH_2PO_4$ and 0.114% $Na_2HPO_4$, pH 7.2) and incubated for 1–5 min at 37°–39° C. The cells are dislodged from the plate by vigorous pipetting and are placed into conditioned stem cell medium (CSCM) to neutralize the trypsin. CSCM is comprised of ~40% Dulbecco's Modified Eagles Medium (DMEM) and ~60% Buffalo Rat liver cell conditioned medium (BRL-CM) containing a total of ~20% fetal calf serum (FCS), β-mercaptoethanol, antibiotics, nucleosides and non-essential amino acids (Smith and Hooper, 1987). The cells are further disaggregated by vigorous pipetting with a fine bore Pasteur pipette. The cells are pelleted by gentle centrifugation and either; 1) left at room temperature overnight followed by subcultured onto new petri plates with fresh CSCM or 2) immediately subcultured onto new petri plates with fresh CSCM.

TABLE 1

COMPARISON OF METHODS OF MAKING
EMBRYONIC STEM CELL LINES

|  | Mice | Evans | Wheeler |
|---|---|---|---|
| Embryo Stage | 3.5 d blast. | 6.5–11 d blasts.[a] | 6.5–10 d hatched blasts. |
| Medium | DMEM | DMEM | DMEM |
| Additives | BME neaa nucleosides | .1% BME neaa — | BME neaa nucleosides |
| Serum | 10% FBS 10% newborn calf | 10% FBS 10% newborn calf Feeder Layer | 18–20% FBS |
| Isolation of ICM | STO | STO | STO or only conditioned medium (CSCM) |
| Maintenance of lines | STO | STO | Conditioned (CSCM) media |
| Purified | no | no | yes |

[a]Manual hatching is disclosed, but it is not clear if all treated blasts are hatched.

2. In Vitro Characterization of ES-Cell Lines

An aspect of the invention is to select a transformed embryonic stem cell in vitro which is likely to produce a chimeric state when introduced into a pig embryo. The selection criteria are based on morphological characteristics of the transformed embryonic stem cell. Generally, morphological characteristics identifiable by inspection of the cell using the light microscope are predictive, although other assays for predictive morphological characteristics are also within the scope of the present invention.

Swine embryonic stem cells of the present invention are translucent, epithelial-like in appearance, and tend to form colonies or nests (clumps) of multilayers as opposed to monolayer growth. (FIGS. 1, 2). Cells have light refractory or round or polygonal cell borders. The cells will also form fluid filled domes with cells exhibiting the currently described ES morphology. The doubling rate of these cells is about 18–36 hours. These characteristics differ little from those reported for mouse embryonic stem cells, but do differ significantly from those reported by Evans. (FIG. 1).

Similarities of swine to mouse embryonic stem cells include that the nucleus to cytoplasmic ratio is approximately 85:15. The nucleus is round and contains several prominent nucleoli. Cell size varies somewhat lines isolated, but most of the stable lines consist of cells with diameters in the range of 8–15 microns.

In Table 2, the differences between the purported ES swine cells of Evans and those of the present invention are set forth. Also, the similarities between the swine cells disclosed herein and the ES cells of mice are described.

TABLE 2

COMPARISON OF CELL MORPHOLOGY OF
MICE AND OF SWINE ES CELLS

| Parameter | Mice | Evans Swine | Swine of the Present Invention |
|---|---|---|---|
| Size | 11–12 μm | "larger than those of the mouse[a]" | 8–15 μm |
| Shape | round | round | round |
| Monolayer | no | yes | no |
| colonies |  |  |  |
| Distinct individual cells can be identified | no | yes | no |
| Cytoplasm (% of cell vol) | 25% | small | 10–25% |
| Nucleus (% cell vol) | 75% | large (no data) | 75–90% |
| Number of nucleoli | 2–4 | 2–4 | 2–4 |
| Teratocarcinoma production in SCID mouse | yes[b] | ? | yes |
| State of embryo cultured | 3.5 d blastocysts | 6.5–11 d hatched blastocysts | 7.5–10 d hatched blastocysts |

[a]Evans relates "a variety of sizes" (column 10 of Evans patent), and sizes varying among cell lines.
[b]Wheeler et al. unpublished results.

3. Teratoma/Teratocarcinoma Assay for Swine Embryonic Stem Cells

It has been established that mouse ES lines form teratoma/teratocarcinomas when introduced into syngeneic host mice. Therefore, this test was incorporated into the screening process during development of porcine ES cell lines. A teratoma is a true neoplasm composed of bizarre and chaotically arranged tissues that are foreign embryologically, as well as histologically, to the area in which the tumor is found. A teratocarcinoma is a teratoma with carcinomatous elements. A carcinoma is a malignant epithelial tumor.

All lines which are truly pluripotent should proliferate, differentiate and form tumors in severe combined immunodeficient mice (SCID) or other immunologically noncompetent animals. Those cell lines which produced tumors are preferable for use in the production of chimeric animals. The selection process is maintained; and 2) only the cells from the tumors or those maintained in number 1), which have maintained their undifferentiated state are utilized in chimera production.

The following protocol was used. Cells were introduced into adult male SCID mice anesthetized with tribromoethanol (0.005g/5 g BW). Testes were exposed through a ventral midline incision. Approximately $2\times10^6$ cells were injected through a 26 gauge needle under the tunica albuginea of one testicle and the other was injected with media only. Three weeks following injection of the cells, animals were euthanized and examined for the presence of tumors. Cells from the tumor were then put into the porcine ES cell culture system. During 7 days of culture, some cells differentiated while others maintained their original embryonic undifferentiated morphology. These undifferentiated colonies were then selected, isolated and grown up for use in the production of chimeras.

4. In Vitro Differentiation of Pluripotent ES-Cells

True ES-cells are induced to differentiate in vitro into ectoderm, mesoderm, and endoderm. There is a concomitant loss during said differentiation of characteristics of undifferentiated ES-cell morphology as described herein for swine, and elsewhere for the mouse.

A method for inducing differentiation in ES-Cells is to culture cell lines such as D49/6-E and M144-B at high density on feeder layers until the cells form small, freefloating cell aggregates. The aggregates are harvested, dispersed, and replated onto 60 mm tissues culture plates coated with 0.1% gelatin.

phology were examined for the presence or absence of staining for vimentin, cytokeratin 18, neurofilaments, glial fibrillar acidic protein, keratin and desmin. (Table 3)

TABLE 3

IMMUNO-STAINING OF EMBRYONIC CYTOSKELETAL STRUCTURAL PROTEINS

| Antibodies | Cell line MW/D49/6-E(T) | Cell line MW/D49/6E(C) | Cell line MW/MI44-B(T) | Cell line MW/M144-B(C) |
|---|---|---|---|---|
| Control | − | − | − | − |
| FITC[2] | − | − | − | − |
| Desmin | + | − | + | − |
| Vimentin | + | − | + | − |
| GFAP[3] | + | − | − | − |
| NF 68,160,200[4] | + | − | + | − |

[1]Letters in parentheses indicate treatment,
T = differentiation induced,
C = untreated control lines,
STO = embryonic fibroblast controls were negative for all antibodies tested;
[2]Fluorescein isothiocyanate control
[3]Glial fibrillary acidic protein
[4]Neurofilament 68kD and 200kD proteins The replated aggregates are cultured without the addition of exogenous agents to the media, until cells are confluent. This is accompanied at a high cell density.

The culture media is changed about every 48 hours and cells are examined daily for evidence of differentiation. Generally, about 30–40% of the cells terminally differentiate under these conditions, that is, reach a recognizable cell type according to criteria known to those of skill in the art. The most commonly observed cell type has a fibroblast type of morphology. If the fibroblast cells are not subcultured, they will eventually develop into adipocyte-like cells about 50 microns in diameter.

Complex cellular structures that are tubular in morphology also appear. In monolayer cultures, some cell structures reach 100 microns in length. These network-like structures resembling capillaries are similar to structures reported in mice. Less commonly, neuronal-like cells also are found in these cultures. The nature of the differentiated cell types is determined by immunofluorescence as described in the methods section herein.

Undifferentiated, pluripotent cells lack the cytoskeletal structural proteins cytokeratin 18 and vimentin, which are only expressed in differentiated cell types. Antibodies are available which are directed against antigenic structures which are indicative of cellular differentiation. (Rudnicki and McBurney, 1987). Examples of these structures include neurofilaments (expressed in ectoderm), glial fibrillar protein (expressed in ectoderm), keratin (expressed in endoderm) and desmin (expressed in mesoderm). Formation of antigen-antibody complexes are indicative of a differentiated state; conversely, absence of an antigen-antibody reaction is evidence for lack of differentiation.

Evidence of pluripotency is provided by differentiation of structures from all the embryonic layers, from a single cell line.

Pluripotent cells lack the cytoskeletal structural proteins, cytokeratin 18 and vimentin, which are only expressed in differentiated cell types. Positive staining against specific antigens, including neurofilaments (expressed in ectoderm), glial fibrillar acidic protein (expressed in ectoderm), keratin (expressed in endoderm) and desmin (expressed in mesoderm), is indicative of cellular differentiation. Replicate colonies of ES-like cells exhibiting undifferentiated mor- 5. In Vivo Differentiation of Pluripotent ES-Cells In vivo differentiation of pluripotent ES-cells was tested by determining the ability of the cells to produce chimeras. To produce chimeras, about 10–20 potentially ES-cells were injected into the blastocoele of 6–7 day old swine embryos. This procedure is similar to that described for production of mouse embryonic chimeras.

In an illustrative embodiment, Meishan swine ES-cells (MW/M175F) were injected into Duroc embryos. Duroc swine are characterized as having red hair and pink skin pigmentation. Meishan swine are characterized as having black hair and black skin pigmentation. These easily visible, inherited traits, allow easy visual screening for presumptive chimeras. In this embodiment, black hair and black pigment appear against a red-brown background if a chimera is produced. In the converse embodiment, Duroc ES-cells are injected into Meishan embryos, and red-brown hair and spots would appear on a black hair, black skin background, if a coat color/skin chimera is present (see Table 4).

TABLE 4

PRODUCTION OF PORCINE CHIMERAS BY MICROINJECTION OF MEISHAN EMBRYONIC STEM CELLS TO DUROC RECIPIENT EMBRYOS

| Recipient Breed | No. Embryos Transferred | No. Live Born Piglets | No. Coat Color Chimeras (%) |
|---|---|---|---|
| Duroc | 18 | 11 | 11 (100) |
| Duroc | 20 | 5 | 4 (80) |
| Meishan | 19 | 9 | 5 (55) |
| Meishan | 7 | 4 | 1 (25) |

In addition to screening for chimeras by observation of the skin of the pigs, screening of genetic markers such as those in the haptoglobin, glucose phosphate isomerase (GPI) and cholesterol 7-alpha hydroxylase systems are available. For example, the Meishan breed has only the B isotype of the GPI polymorphism, whereas the Duroc breed has both the A and B isotype. Appearance of the A and B isotype in a Meishan pig, is evidence of chimerism.

The cholesterol-7α-hydroxylase 4 allele gene system is illustrated by a Taq I polymorphism at the cholesterol-7α-hydroxylase gene locus in Meishan, Duroc and Yorkshire breeds of swine. The polymorphic bands (illustrating 2 alleles) for the Meishan breed appear at ~2.5 and ~4 kb. The polymorphic bands (illustrating 2 alleles) for the Duroc and Yorkshire breeds appear at ~2.8 kb and ~5.0 kb. The 2.5 and 4 kb alleles are breed specific only for the Meishan breed. The 2.8 and 5.0 kb alleles are breed specific only for the Duroc and Yorkshire breeds. Appearance of 2 bands (one characteristic of the Meishan breed and one characteristic of the Duroc or Yorkshire breeds) or 3 bands in any combination or 4 bands is evidence of chimerism. Restriction fragment length polymorphisms (RFLP's) are analyzed by Southern analysis, phosphoimagery and autoradiography.

6. Uses for Embryonic Stem Cells a) Xenografts (xenotransplantation)—cells, tissues or organs with exogenous major histocompatibility or other foreign or endogenous antigens and/or genes that will decrease rejection by the host organism of these transplanted materials may be produced. Exogenous foreign or homologous DNA is transferred to porcine ES cells by electroporation, exposure to calcium phosphate, microinjection, lipofection, retro- or other viral or microbial vector or other means. The ES cells are screened for incorporation for this DNA or expression of antigens, directly transferred to embryos to produce chimeras, or used in nuclear transfer systems to clone pigs. These cells, tissues and organs are harvested from embryos, fetal, neo-natal or resulting adults for xenotransplantation. In this manner, humanized-pig kidney for kidney transplants are contemplated.

Production of differentiated cells for replacement, repair or augmentation of damaged, non-functional, or impaired cells or tissues are another use. Exogenous foreign or homologous DNA are transferred to porcine ES cells by electroporation, calcium phosphate, microinjection, lipofection, retro- or other viral or microbial vector or other means. The ES cells are screened for incorporation for this DNA, directly transferred to embryos to produce chimeras, or used in nuclear transfer systems to clone pigs. These cells and tissues are harvested from embryos, or resulting adults for use to repair or augment some defect. For example, pig fetuses, and neonates, may be used in treating Parkinson's patients, persons who had heart attacks, or spinal cord injuries.

b. Production of specific proteins or other biological molecules—pharmaceuticals, diagnostics, antibodies, used in manufacturing or processing, as food supplements of additives and the like, are produced using ES cells. Exogenous foreign or homologous DNA are transferred to porcine ES cells by electroporation, calcium phosphate, microinjection, lipofection, retro- or other viral or microbial vector or other means. The ES cells are screened for incorporation for this DNA, or are directly transferred to embryos to produce chimeras, or are used in nuclear transfer systems to clone pigs. These proteins or other molecules are harvested from pig embryos, fetuses, neonates or resulting adults for further purification. For example, human blood clotting factor IX may be produced in pig milk for treatment of hemophilia.

Transgenic swine may be produced with altered tissue or milk proteins which may be collected for commercial or experimental use.

Examples of the following pharmaceutical, therapeutic processing, manufacturing or compositional proteins include: blood proteins (clotting factors VIII and IX, complement factors or components, hemaglobins or other blood proteins and the like), hormones (insulin, growth hormone, thyroid hormone, gonadotrophins, PMSG, trophic hormones, prolactin, oxytocin, dopamine, catecholamines and the like, growth factors (EGF, PDGF, NGF, IGF's and the like), cytokines (interleukins, CSF, GMCSF, TNF, TGFα and β and the like), enzymes (tissue plasminogen activator, streptokinase, cholesterol biosynthetic or degradative, digestive, steroidogenic, kinases, phophodisterases, methylases, de-methylases, dehydrogenases, cellulases, proteases, glycosolases, lipases, phospholipases, aromatase, cytochromes adenylate or guanylate cyclases and the like), hormone or other receptors (LDL, HDL, steroid, protein, peptide, lipid or prostaglandin and the like), binding proteins (steroid binding proteins, growth hormone or growth factor binding proteins and the like), immune system proteins (antibodies, SLA or MHC genes, antigens (bacterial, parasitic, viral, allergens and the like), translation or transcription factors, onco-proteins or protoonco-proteins, milk proteins (caseins, lactalbumins, whey and the like), muscle proteins (myosin, tropomyosin and the like).

In a typical situation, the nucleotide segment encodes a precursor form of the protein ultimately harvested from the transgenic pigs. Of course, certain products are not recoverable for production from certain tissues. The method disclosed herein for determining what cell types express a certain construct will be useful in determining what is suitable.

| EXAMPLES OF PROTEINS THAT ARE RECOVERABLE FROM TRANSGENIC PIG BODY FLUIDS | |
|---|---|
| Body Fluids | Protein |
| Milk[a] (almost all proteins) | Factor IX Lactoferrin Lactalbumin EGF IGF FGF NGF |
| Urine (small proteins on the order of 10–100 aa) | (Gonadotrophins) FSH LH Oxytocin PRL |
| Blood | Clotting factors Hemoglobin Plasmin TPA |
| Saliva | EGF Growth factors Digestive enzymes |

[a]if using pig milk as a protein source, mammary specific promoter is needed for the transgene, for example, α-lactalbumin c. Enhance genetic traits in livestock—Porcine ES cells are used to improve disease resistance; growth rate and efficiency; milk production, quality and composition; carcass quality and composition; body composition; reproductive efficiency and performance. Further, improved performance by controlling expression of a specific gene during development and growth and adulthood, including autoimmunization against pathogens, increased secretion of growth promotants, stimulation of reproductive processes including lactation is contemplated. Genetically-engineered individuals resulting from porcine ES cells serve as founder animals for new breeds or strains of swine. For example, altered milk protein composition allows for increased survivability of piglets and increased growth.

Removing or altering deleterious alleles, genes, or DNA sequences is affected using homologous recombination. Specific DNA sequences are removed, introduced or altered to manipulate the biology of the individual. Genetically-engineered individuals resulting from porcine ES cells serve as foundation animals for new breeds or strains of swine. For example, removing the gene encoding the enzyme responsible for producing the hormone that causes boar taint will yield an animal not showing that condition.

d. Production of "genetically engineered" identical offspring is accomplished by the transfer of ES cell nuclei to embryonic cells or unfertilized oocytes, such that resultant cell lines, tissues, organs or offspring contain all or part of the genetic material of the transferred nucleus or nuclei. These individuals are useful for increasing product uniformity; gene mapping, histocompatibility; propagating specific desirable or genetically (DNA-transformed) genotypes, providing large numbers of genetically identical cells, tissues, organs and animals for transplantation and research purposes.

ES cells from specific cell lines, either with or without an exogenous gene or genes, are transferred by micromanipulation to foreign cytoplasm such as enucleated oocytes or embryonic cells. The resultant cells are cultured to establish new lines, used to form chimeric embryos, tissues, and/or organs or transferred to surrogate mothers for production of genetically engineered offspring. Transfer of multiple cells or a single ES cell or nucleus to an enucleated oocyte or embryonic cell is accomplished through micromanipulation. Fusion of the transferred cell or nucleus is accomplished with electropulses, exposure to fusion agent such as Sendai virus or polyethylene glycol, or by exposure to ionophores that alter the ionic fluxes of the cell membranes. Genetically-engineered individuals resulting from porcine ES cells serve as foundation animals for new breeds or strains of swine. For example; ES cells carrying a transgene may be fused to enucleated oocytes to produce cells with identical nuclear DNA for production of cloned cells, tissues, organs (kidneys transplant) or animals.

7. Gene Transfer

Cell lines which have produced tumors in SCID mice are preferred as vectors to carry transgenes into the chimeric animals. The transgene may be carried by a variety of methods into the cell. These methods include electroporation, microinjection, lipofection, retroviral infection and calcium phosphate. The cells are screened with the antibiotic G418 (when constructs contain neo gene) or other appropriate screening drug or compound. The remaining colonies after screening are cloned and checked for incorporation of the transgene via methods known to those of skill in the art, including PCR, Southern, Northern or Western analysis.

8. Production of Human Clotting Factor IX

The production of human clotting factor IX (FIX) in the milk of transgenic swine via embryonic stem cells is accomplished by the following protocol. The human clotting factor IX protein encoding sequence is excised from the FIX cDNA (Clark et al., Expression of human anti-hemophilic factor IX in the milk of transgenic sheep. BIOTECHNOLOGY, Vol. 7: 487–492, 1989) and ligated to a mammary specific promoter (such as the alpha lactalbumin promoter) to produce the transgene construct. This construct is electroporated into the stem cells. A gene for a selectable marker such as neo is coelectroporated so that following a recovery period, the transgenic cells will be selected by adding G418 to the media which will kill all cells that have not incorporated and are not expressing the neo gene. These cells are injected into porcine embryos to form chimeras or used for cloning to directly produce transgenic animals. The animals are screened using the transgene as a probe and mRNA from mammary tissue biopsy is tested for appropriate expression of the FIX gene. The transgenic females are bred and milked and the FIX extracted.

MATERIALS AND METHODS: Collection of Swine Embryos and Isolation of Swine ES-like Cells.

1. Control of ovulation and embryo collection: Sows were checked for estrus twice daily. The donors were inseminated at estrus. Embryos were collected on days 5.5–8.0 as expanded or hatched blastocysts.

2. Subculture of STO cells: When plates of STO cells became or approached confluence (80%), they were subcultured. Medium was removed from the plates, and 2 ml of freshly thawed (thaw in 37° C. $H_2O$ bath) trypsin EDTA (0.25%; 0.04%) added. Plates were placed in a 38° C. incubator for 5 minutes. Trypsin was neutralized by adding 2 ml of serum-DMEM (sDMEM, complete medium; warmed in the 37° C. $H_2O$ bath) to each plate. Cells were then vigorously pipetted to form a single cell suspension. Fresh medium was added to effect a 1:2–1:10 dilution. The dilution ratio is adjusted to the degree of confluence and number of the plates of cells. Plates were gently swirled to ensure uniform plating. Plates were then placed in a 38° C., 5% $CO_2$ incubator. Medium was changed every 2 days with cells growing to confluence (80%) within 2–5 days, depending upon seeding density.

3. Preparation of feeder layers: STO cells were treated two days prior to use as feeder layers. Using plates of STO cells that were nearly confluent (generally one day prior to being confluent), medium was aspirated, and carefully replaced with 2–4 mls of a 10 ug/ml solution of Mitomycin C (Sigma Chemical Co.) and returned to 38° C. incubator for 2–3 h. At this time, mitomycin C solution was removed by washing each plate 2–3× with 5 ml of sterile PBS, pH 7.2. Medium was replaced with 10 mls of sDMEM and plates returned to the incubator at 38° C. for 24 h. After 24 h the medium was replaced with fresh medium and again when used as a feeder layer. Feeder layers can be kept up to ten days before use.

4. Embryo culture: Embryos were washed 3 times in modified Whitten's or other embryo culture medium and placed individually into culture vessels containing 1) a reformed feeder layer of fibroblasts (STO cells) or 2) no feeder layer; with either stem cell Modified Whitten's medium (SCM; with L-glutamine, 4500 mg glucose/L containing 1.5 g/L of $NaHCO_3$ at pH 7.4, Sigma Chemical CO, St., Louis, Mo.) with 20% fetal calf serum, penicillin-streptomycin, $10^{-4}$M 2-mercapoethanol, and non-essential amino acids (for feeder layers), or stem cell medium (SCM) for a feeder layer, or CSCM (with or without feeder layers).

ES cell culture medium (SCM) consisted of Dulbecco's modified Eagle's medium (DMEM; containing L-glutamine, 4500 mg glucose/L) with 0.1 mM 2-mercaptoethanol, 50 IU penicillin/L, 50 µg streptomycin/L, 10 mM/L MEM non-essential amino acids (Robertson, 1987) and 20% FBS.

After the embryos are collected, they are washed 3 times with fresh culture medium to dilute contaminants from the tract. If embryos have not hatched, they are transferred to micro drops of W-2 media under oil and culture to hatching. This will only occur if 6-day embryos or younger are flushed out. When hatched blastocysts are obtained, they are transferred to an individual well in a 24 well plate. Each well should contain 1 ml media (Stem Cell Media, SCM) if using STO feeder layers, and Conditioned Stem Cell Media (CSCM) if not using a feeder layer. Initial stages of culture were carried out. After 24–48 h of culture the embryos hatched from the zone pellucida and attached to the culture dish.

5. Stem cell isolation and culture: Embryonic stem cells were isolated from the attached embryos and maintained in culture by the following protocol. The inner cell mass (ICM) enlarges during the first few days of culture. After enlargement, the ICM was dislodged from the underlying cells and washed through two changes of calcium/magnesium-free PBS. The ICM was then transferred to a 50 μl drop of trypsin solution (0.25% trypsin, 0 4% EDTA in $Ca^{++}$, $Mg^{++}$-free phosphate buffered saline, PBS; 1.0% NaCl, 0.025% KCl, 0.025% $KH_2PO_4$, and 0.114% $Na_2PO_4$, pH 7.2) and incubated for 1–5 minutes at 38° C.

The cells were disaggregated with a fine Pasteur pipette. The contents were then transferred to a fresh drop of CSCM with 20% FCS in a fresh culture vessel with or without a feeder layer. The cultures were inspected daily for the appearance of nests of round stem cells which appear after 7–8 days (range 2–21 days) culture. Colonies were dissociated from the feeder layers, as described above, treated with trypsin and passed to fresh feeder layers. In successful cultures, small nests of stem cells appear after 2–3 days of subculture. These nests were isolated, dispersed and plated on fresh culture vessels with or without feeder layers. The cells at this stage require subculture every 3–10 days depending on the growth rate. Cells had spent media replaced with fresh media every 2–3 days. To preliminarily characterize the pluripotent nature of ES-cell lines we used microscopic observation of undifferentiated morphology. ES-cells are typically small and rounded, possessing large dark nuclei which contain one or more prominent nucleoli.

ES cells were purified, as described herein, from feeder cells or from differentiated porcine cells (lines were developed entirely in conditioned medium (CSCM) alone). Further characterization requires indirect immunofluorescent staining of ES-cells for lack of the cytoskeletal structural proteins, cytokeratin 18 and vimentin, which are only expressed in differentiated cell types. In vitro differentiation of pluripotent ES-cells into endoderm, ectoderm or mesodermwith concomitant loss of typical undifferentiated ES-cell morphology and positive staining with anti-cytokeratin 18 and anti-vimentin antibodies may be induced.

6. Culture of embryonic stem cells: Once established, stem cells grow rapidly, dividing every 18–36 hours. The cells should be kept at relatively high densities to ensure that a high rate of cell division is maintained as this minimizes the level of spontaneous differentiation. The cultures were re-fed daily, or according to the acidity of the medium, and subcultured at 3–4 day intervals. Cells were routinely grown in the same medium (CSCM) as for the original embryos from which they were derived.

The stem cells were passed when the plates approached confluence. The cells were re-fed 2–3 hours prior to passage to improve the cell viability. The medium was aspirated and the cell surface washed with 5 ml of sterile PBS. The PBS was replaced with 0.5–3 mls of trypsin EDTA and incubated at 38° C. for 1–5 minutes. The plate was then removed from the incubator and the suspension pipetted vigorously using a sterile plugged Pasteur pipette. After pipetting the cell suspension was checked visually under low-power (40×) to ensure that it was relatively free of cellular aggregates. The cells were pelleted in a centrifuge tube at 1000× g for 5 minutes the supernatant aspirated and the cells resuspended in 10 ml of medium (CSCM). Finally, the cell density was determined and the cell suspension re-plated onto feeder plates ($1-2 \times 10^6$ cells per 100 mm plate) containing 10–12 ml of complete medium.

7. Production of chimeras: After stable ES-cell lines are established, they are used to produce chimeric swine embryos. This is to test the ability of the cell lines to participate in the formation of the resultant offspring. Morulas or blastocysts are recovered, as described above, and placed in 100 μl of PBS under oil. The embryos have 5–50 ES-cells placed into the blastocoele cavity by means of a glass injection needle attached to a micromanipulator. After injection, the embryos are immediately transferred back to suitably prepared recipient gilts. Initial chimeras were designed so that they were easily screened using coat color markers (i.e., Meishan X Duroc). Resultant individuals have patches of different color skin and hair derived from each of the embryonic cell lineages.

8. Production of Chimeras and Clones via Nuclear Transfer: Chimeras are produced by aggregation of ES cells with pre-implantation embryos of the following stages: one-cell, two-cell, four-cell, eight-cell, 16-cell, 32-cell, morula, blastocyst, and hatched blastocyst. Chimeras are also produced by injection of ES cells with pre-implantation embryos of the following stages: one-cell, two-cell, four-cell, eight cell, 16-cell, 32-cell, morula, blastocyst, and hatched blastocyst.

Nuclear transfer offspring or clones are produced by fusion or injection of ES cells with enucleated, preimplantation embryonic cells of the following stages of embryo: oocytes, one-cell, two-cell, four-cell, eight-cell, 16-cell, 32-cell, morula, blastocyst, and hatched blastocyst.

In vivo differentiation of pluripotent ES-cells was confirmed by their ability to participate in the formation of chimeric offspring. Morula, blastocyst and expanded blastocyst stage embryos were placed in 100 μl of PBS under oil. The embryos were grasped by a fine glass holding pipette attached to a micromanipulator (Narashige Inc., Tokyo, Japan). Five to 20, range one to 30, ES-cells were placed into the cell mass (morula) or into the blastocoele cavity (blastocyst and expanded blastocyst) by means of a glass injection needle, 25–30μ in diameter, which was attached to a micromanipulator. After injection, the embryos were immediately transferred to recipient gilts which had been in estrus 24 h after the embryo donor.

Chimeras were designed so that they could be easily screened using coat color markers (i.e., Meishan and Duroc). Chimeric embryos were produced using two coat color markers: Meishan (black hair with black skin pigmentation) ES-cells were injected into Duroc (red-brown hair with pink skin pigmentation) embryos. These combinations allowed for easy visual detection of chimeric animals. Informative genetic markers were used to screen chimeric animals such as polymorphism in the glucose phosphate isomerase (GPI) and the cholesterol-7α-hydroxylase gene systems.

9. Breeds of swine: The Meishan breed is from the lake Taihu region near Shanghai. Taihu pigs appear to be the most prolific in China. The region is characterized as temperate, with temperature averaging 15.7° C. and ranging from an annual low of −9.0° C. to an annual high of 38.2° C. The Chinese Taihu breeds of pig are highly prolific and attain puberty at an early age, but have poor growth rates and carcass quality. Chinese Meishan pigs range from light grey to dark black in color with varying degrees of white spots. Meishan pigs characteristically have white feet and hooves, extremely wrinkled faces and large, pendulous ears. Domestication of the pig in China dates back to a least 3,000 B.C. and, over time, Chinese pigs have contributed to the development of world pig breeds. A large number of pigs from South China were imported into the Roman Empire in the 3rd century B.C. and used to improve European breeds. From the 16th through the 18th century A.D., pigs from South China were imported to England and used in the development of modern breeds, particularly the Yorkshire and Berkshire. By the end of the 18th century, breeds with Chinese ancestry had replaced almost all indigenous English breeds.

The Berkshire and Yorkshire breeds in the United States originated with importations from England in 1823 and 1893, respectively. Chinese pigs, introduced into 19th century America, also played a role in the formation of the Poland China and Chester White breeds. Importation of promising foreign breeds has a long tradition in livestock production, with Landrace (first imported from Denmark in 1934) the most recently introduced pig breed that has contributed substantially to U.S. pork production.

The Duroc breed is a totally American breed and dates back to the 1870's when a combination of the Jersey Red from New Jersey and the Duroc from New York formed a breed known as Duroc-Jersey, later to become know as simply the Duroc. The Duroc is a very durable breed and has been shown to have high growth rate and good marbling characteristics. These two characteristics, fast growth and carcass quality, plus a strong confirmation has helped to place the Duroc at the top (along with Yorkshire) of purebred registrations in the U.S. Durocs are solid red in color, varying from light to dark, and have medium-sized, pendulous ears.

10. Media formulations are shown in Tables 5–14.

TABLE 5

MEDIA

| MEDIA LABEL | DESCRIPTION | CELL TYPE |
|---|---|---|
| DMEM | Basal medium for all cell culture | — |
| sDMEM | DMEM + FBS + PEN/STREPT | BRL + STO |
| BRL-CM | sDMEM harvested from BRL cells used to make CSCM | — |
| SCM | [DMEM + FBS] + each additive* | embryonic stem cells on feeder layers |
| CSCM | [BRL-CM + FBS + each additive*) + SCM | embryonic stem cells, no feeder |

*Additive = β-mercaptoethanol, antibiotics stock, nucleosides stock, and MEM non-essential amino acids
PEN = penicillin
STREPT = streptomycin

TABLE 6

DULBECCO'S MODIFIED EAGLE'S MEDIUM (DMEM) FOR THE CULTURE OF ANIMAL CELLS IN AN IN VITRO ENVIRONMENT

| Ingredient | mM | gm/L |
|---|---|---|
| Dulbecco's modified Eagle's medium (DMEM) (Sigma-Hybrimax D 6655) containing: | — | 13.4 |
| NaCL | 110.0 | 6.4 |
| Na$_2$HPO$_4$ | 0.80 | 0.109 |
| Glucose | 25.0 | 4.5 |
| Phenol red-Na | 0.043 | 0.016 |
| L-Arginine | 0.39 | 0.084 |
| L-Cystine | 0.40 | 0.063 |
| L-Glutamine | 4.01 | 0.584 |
| Glycine | 0.40 | 0.030 |
| L-Histidine | 0.271 | 0.042 |
| L-Isoleucine | 0.80 | 0.105 |
| L-Leucine | 0.80 | 0.105 |
| L-Lysine | 1.01 | 0.146 |
| L-Methionine | 0.20 | 0.030 |
| L-Phenylalanine | 0.40 | 0.066 |
| L-Serine | 0.40 | 0.042 |
| L-Threonine | 0.80 | 0.095 |
| L-Tryptophan | 0.08 | 0.016 |
| L-Tyrosine | 0.60 | 0.104 |
| L-Valine | 0.80 | 0.094 |
| Choline chloride | 0.03 | 0.004 |
| Folic acid | 0.01 | 0.004 |
| myo-Inositol | 0.04 | 0.007 |
| Niacinamide | 0.04 | 0.004 |
| D-Pantothenic acid | 0.02 | 0.004 |
| Pyridoxal | 0.02 | 0.004 |
| Riboflavin | 0.001 | 0.0004 |
| Thiamine | 0.012 | 0.004 |
| Calcium chloride | 1.80 | 0.265 |

TABLE 6-continued

DULBECCO'S MODIFIED EAGLE'S MEDIUM (DMEM) FOR THE CULTURE OF ANIMAL CELLS IN AN IN VITRO ENVIRONMENT

| Ingredient | mM | gm/L |
|---|---|---|
| Ferric nitrate | 0.0002 | 0.0001 |
| Magnesium sulfate | 0.83 | 0.100 |
| Potassium chloride | 5.37 | 0.400 |
| NaCHO$_3$ | 17.6 | 1.5 |
| Distilled water up to | | 1 L | pH adjusted to 7.3 with 1 N HCl, filter sterilized, and stored up to 2 weeks at 4° C.
This is a general tissue culture medium for the maintenance and propagation of animal cells in an in vitro environment.

TABLE 7

PHOSPHATE BUFFERED SALINE (PBS) FOR CELL CULTURE MANIPULATION

| Ingredient | mM | gm/L |
|---|---|---|
| NaCL | 171.1 | 10.0 |
| KCl | 3.35 | 0.25 |
| Na$_2$HPO$_4$ | 6.25 | 0.75 |
| KH$_2$PO$_4$ | 1.84 | 0.25 |
| Distilled water up to | | 1 L |

Adjust pH to 7.3 with 1 N HCl, and filter sterilize to prevent contamination of cell cultures.
This is a general purpose saline solution used for various cell culture techniques to maintain cell integrity.

TABLE 8

ANTIBIOTIC STOCK SOLUTION FOR ADDITION TO CELL CULTURE MEDIUM TO PREVENT BACTERIAL CONTAMINATION

| Ingredient | Amount |
|---|---|
| Penicillin G-potassium salt | 500 units |
| Streptomycin sulfate | 5 mg |
| Phosphate buffered saline (PBS; Table 7) | 10 ml |

Stored at 4° C. and replaced weekly.
Penicillin and Streptomycin help prevent bacterial proliferation in cell culture in vitro after contamination has occurred.

TABLE 9

TRYPSIN-EDTA SOLUTION FOR DISSOCIATION OF CELLS IN TISSUE CULTURE

| Ingredient | mM | gm/L |
|---|---|---|
| Trypsin powder-porcine (1000–1500 units/mg) | — | 2.5 |
| Ethylenediaminetetraacetic acid-disodium salt (EDTA) | 1.10 | 0.4 |
| NaCl | 119.8 | 7.0 |
| Na$_2$HPO$_4$ | 2.50 | 0.3 |
| KH$_2$PO$_4$ | 1.76 | 0.24 |
| KCl | 4.96 | 0.37 |
| Glucose | 5.56 | 1.0 |
| Tris (hydroxymethyl aminomethane) | 24.80 | 3.0 |
| Phenol Red | 0.03 | 0.010 |
| Distilled water up to | — | 1 L |

Filter sterilized and aliquoted into 10 ml tubes, then frozen at −20° C.
Trypsin is an enzyme protease that dissociates cell clumps into a single cell suspension for passage of cells in tissue culture. The frozen solution is thawed and warmed to 37° C. before use.

TABLE 10

STO FIBROBLAST CELL CULTURE MEDIUM FOR THE MAINTENANCE AND PROLIFERATION OF STO CELLS IN VITRO

| Ingredient | Volume (ml) |
|---|---|
| DMEM (Table 6) | 449.0 |
| Pen-Strep stock (Table 8) | 1.0 |
| Fetal bovine serum (FBS; heat inactivated) | 50.0 |

Filter sterilized, stored at 4° C., and used within 2 weeks. Warm to 37° C. before use with STO cells.
This medium allows the growth and maintenance of the transformed fibroblast cell line STO in tissue culture.

TABLE 11

MOUSE ES CELL CULTURE MEDIUM FOR THE ISOLATION AND MAINTENANCE OF MURINE ES CELLS IN VITRO

| Ingredient | mM | gm/L | Volume (ml) |
|---|---|---|---|
| DMEM (Table 6) | — | — | 80.0 |
| Fetal bovine serum (FBS; beat inactivated) | — | — | 20.0 |
| Antibiotic stock (Table 8) | — | — | 1.0 |
| Mercaptoethanol-β stock (7 µl in 10 ml PBS) | — | — | 1.0 |
| Non-essential amino acids (Sigma-M 7145, St. Louis) Containing: | — | — | 1.0 |
| L-Alanine | 10.0 | 0.89 | — |
| L-Asparagine | 10.0 | 1.50 | — |
| L-Aspartic acid | 10.0 | 1.33 | — |
| L-Glutamic acid | 10.0 | 1.47 | — |
| Glycine | 10.0 | 0.75 | — |
| L-Proline | 10.0 | 1.15 | — |
| L-Serine | 10.0 | 1.05 | — |
| Nucleosides stock (Table 12) | — | — | 1.0 |

Filter sterilized, stored at 4° C., and used within 2 weeks. Warm to 37° C. before use with ES cells.
This medium allows the isolation and proliferation of embryonal cell lines from mouse blastocysts when in co-culture with mitotically-inhibited embryonic fibroblast cells.

TABLE 12

NUCLEOSIDE STOCK SOLUTION FOR ADDITION TO TISSUE CULTURE MEDIUM

| Ingredients | mM | mg/100 ml |
|---|---|---|
| Adenosine | 3.0 | 80.0 |
| Guanosine | 3.0 | 85.0 |
| Cytidine | 3.0 | 73.0 |
| Uridine | 3.0 | 73.0 |
| Thymidine | 1.0 | 24.0 |
| Distilled water | — | 100 ml |

Filter sterilized, aliquoted, stored at 4° C., and warmed to 37° C. to resolubilize before addition to the culture medium.
The addition of nucleosides to the culture medium of rapidly growing cell cultures aids in cell proliferation.

TABLE 13

CRYOPRESERVATION (FREEZING) MEDIUM FOR EMBRYONIC CELLS

| Ingredient | mM | Volume |
|---|---|---|
| DMEM (Table 6) | — | 60 ml |
| Dimethyl Sulfoxide (DMSO) | 0.781 | 20 ml |
| Fetal bovine serum (FBS) | — | 20 ml |

TABLE 13-continued

CRYOPRESERVATION (FREEZING) MEDIUM FOR EMBRYONIC CELLS

| Ingredient | mM | Volume |
|---|---|---|

Filter sterilized, aliquoted 0.5 ml into 1.0 ml freezing vials, stored at −20° C. Thaw before addition of 0.5 ml cell suspension, cool slowly to −70° C. then freeze at −196° C.
The cryopreservation solution prevents formation of ice crystals in cells and thus allows high cell visibility.

TABLE 14

MODIFIED WHITTEN'S MEDIUM

| Ingredient | MW | gm/l | gm/100 ml | mM | mOsm |
|---|---|---|---|---|---|
| NaCl | 58.44 | 5.14 | 0.514 | 88 | 176 |
| KCl | 74.55 | 0.36 | 0.036 | 4.8 | 9.6 |
| $KH_2PO_4$ | 136.1 | 0.16 | 0.016 | 1.17 | 2.34 |
| $MgSO_4$ | 246.5 | 0.29 | 0.029 | 1.17 | 2.34 |
| $NaHCO_3$ | 84.01 | 1.9 | 0.19 | 22.6 | 45.2 |
| NaPyruvate | 110.0 | 0.035 | 0.0035 | 0.3 | 0.6 |
| CaLactate | 109.1 | 0.53 | 0.053 | 4.8 | 14.4 |
| Glucose | 180.2 | 1.0 | 0.1 | 5.5 | 5.5 |
| NaLactate | ** | 3.7 ml | 0.37 ml | 19.8 | 39.6 |
| K Pen | | 0.08 | 0.008 | — | — |
| Strep $SO_4$ | | 0.05 | 0.005 | — | — |
| Phenol Red | | 1 ml of 1% soln. | 0.1 ml of 1% soln. | | |

**MW is 112.1 anhydrous; 3.7 ml 60% syrup/l = 39.6 mOsm.
(3.7 ml/112.1 = 0.033 × .6 = 0.0198 Osm = 19.8 mOsm.)

11. Immunofluorescence as a Measure of Differentiation in Pluripotent Porcine Embryonic Stem Cells

MATERIALS

ES cell lines to test several fetal pigs

PBS+0.1% BSA

8 Chamber Tissue-Tek slides

3% paraformaldehyde in 0.1M. Sorensen's Phosphate buffer

Primary antibodies
  Monoclonal Anti-Cytokeratin-ICN
  Monoclonal Anti-GFAP-ICN
  Monoclonal Anti-Neurofilament 68-ICN
  Monoclonal Anti-Neurofilament 170-ICN
  Monoclonal Anti-Neurofilament 200-ICN
  Monoclonal Anti-Desmin-ICN
  Monoclonal Anti-Vimentin-ICN Secondary antibody FITC-ICN 37° humidified incubator L. R. White embedding media

POSITIVE CONTROL

1. Remove the brain, heart, intestine, and skeletal muscle from several fetal pigs, cut in 1 mm sections and place in glass vials.
2. Wash three times in Sorensen's buffer. Remove final buffer wash and flood vial with 3% paraformaldehyde. Fix for a minimum of 1 hour.
3. Remove fixative and wash with buffer 3 times, 5 minutes each, to remove excess fixative.
4. Dehydrate in a series of ethanol changes, 10%, 25%, 50% and three times in 70% ethanol, 10 minutes each change.
5. After the third 70% ethanol change, remove ½ of the ethanol and replace with an equal volume of L. R. White embedding media.
6. Place vial on a rotary mixer at slow speed overnight.
7. Next day, remove ½ of the White/ethanol mixture and add an equal volume of L. R. White. Let set 1 hour. Repeat 1 time.

8. Invert vial on several thicknesses of kim wipes and tap to remove all sections.
9. Put a drop of L. R. White in the tip of each BEEM capsule, and using a wooden applicator stick, pick up the sections and place in the middle of each capsule, 1 section/capsule.
10. Fill the capsules with L. R. White, taking care not to create air bubbles.
11. After all capsules are prepared, place in a 56° oven to polymerize the L. R. White. Leave in oven overnight.
12. Next day, test capsules to see if polymerization has occurred. If it has, remove block from capsule, trim and section. If it has not, leave in oven 24 hours.
13. Place sections on non-fluorescing slide, and draw circle around section using PAP pen.
14. Drop 20 μl of primary antibody on each section. Place in incubator for 30 minutes.
15. Remove primary antibody and wash 3 times with PBS. Check for autofluorescence.
16. Drop 20 μl of secondary antibody on each section. Place in incubator for 30 minutes.
17. Remove secondary antibody and wash 3 times with PBS. Allow to dry and view, then record results.

PREPARING CELLS FOR IMMUNOFLUORESCENCE

1. Subculture when cells are 80–90% confluent and make normal dilution of cell suspension.
2. Using a 1 ml pipet, transfer 0.3 ml cell suspension to each of the 8 chambers in the Tissue-Tek slide. Make a chamber for each of the following:
   a. each antibody
   b. blank—check for auto-fluorescence
   c. FITC only
3. After the desired number of slides are prepared, place in incubator and culture until monolayer is confluent or until desired cells are apparent. (If culture beyond 2 days, change media.)
4. When cells are ready, remove media and wash monolayer with PBS+0.1% BSA.
5. Remove final buffer wash, and flood chamber with 3% paraformaldehyde. Fix for minimum of 1 hour, but can leave on until ready to add antibody.

PRIMARY ANTIBODY

1. Remove fixative and wash with 0.1% BSA buffer 3 times, 10 minutes. (Leave last buffer wash on for 1 hour.)
2. Calculate volume of primary antibody needed. Each chamber will need 50 μl. Then prepare a 1:50 dilution using this volume. (Ex: If you need 500 μl of each Ab, then dilute 10 μl AB in 490 μl 10.1% BSA buffer.)
3. Remove final buffer wash and add 50 μl of antibody to each chamber. Place in incubator for 30 minutes.
4. After incubation, flood chamber with buffer and let set 10 minutes.
5. Calculate volume of FITC needed and prepare a 1:200 dilution.
6. Remove antibody and buffer and wash 3 times in 0.1% BSA buffer.
7. Can check for auto-fluorescence at this time if you are not preparing a blank.
8. Add 50 μl FITC to each chamber and incubate for 30 minutes.
9. After incubation, flood each chamber with 0.1% BSA buffer and let set 10 minutes.
10. Remove FITC and buffer and wash 3 times with buffer. After final wash, invert slide and let dry.
11. When dry, remove chambers and gasket, then observe for fluorescence and record results.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

REFERENCES

The references listed below are incorporated herein by reference to the extent that they supplement, explain, provide a background for, or teach methodology, techniques, and/or compositions employed herein.

Axelrod, H. R., 1984, Embryonic stem cell lines derived from blastocysts by a simplified technique, Dev. Biol. 101:225–228.

Bradley, A., Evans, M., Kaufman, M. H., Robertson, E. 1984. Formation of germline chimaeras from embryo-derived teratocarcinoma cell lines. Nature 309:255–256.

Doetschman et al., 1988, Establishment of hamster. blastocyst-derived embryonic stem (ES) cells, Dev. Biol. 127:224–227.

Evans, 1990, WO90/03432, Handyside et al. 1987. Towards the isolation of embryonal stem cell lines from the sheep, Roux's Arch. Dev. Biol. 196:185–190.

Evans, M. J. and Kaufman, M. H. 1981. Establishment in culture of pluripotential cells from mouse embryos. Nature 292:154–156.

Gordon J. W., Scangos, G. A., Plotkin, D. J., Barbosa, J. A., Ruddle, F. H. 1980. Genetic transformation of mouse embryos by microinjection of purified DNA. Proc. Natl. Acad. Sci. USA 77:7380–7384.

Gossler, A., Doetschman, T., Korn, R., Serfling, E., Kemler R. 1986. Transgenesis by means of blastocyst-derived embryonic stem cell lines. Proc. Natl. Acad. Sci. USA 83:9065–9069.

Hammer, R. E., Pursel, V. G., Rexroad, C. E., Jr., Wall, R. J., Bolt, D. J., Ebert, K. M., Palmiter, R. D., Brinster, R. L. 1985. Production of transgenic rabbits, sheep and pigs by microinjection. Nature 680–683.

Martin, G., 1981, Isolation of a pluripotent cell line from early mouse embryos cultured in medium conditioned by teratocarcinoma stem cells, PNAS 78:7634–7638.

McWhir, J., 1989, Embryonic cell lines in farm animals, Ph.D. Thesis, Univ. of Calgary.

Murray, J. D., Nancarrow, C. D., and Ward, K. A. 1988. Controlled production of sheep growth hormone in transgenic mice and sheep. 11th InternationalCongress on Animal Reproduction and Artificial Insemination 5:20.

Notarianni et al., Maintenance and differentiation in culture of pluripotential embryonic cell lines from pig blastocysts, J. Reprod. Fert. Suppl. 41 1990, 51–56.

Piedrahita, J. A., Anderson, G. B., BonDurrant, R. H. 1990b. On the isolation of embryonic stem cells: Comparative behavior of murine, porcine and ovine embryos. Therio. 34:879–901.

Piedrahita, J. A., Anderson, G. B., BonDurrant, R. H. 1990a. Influence of feeder layer on the efficiency of isolation of porcine embryo-derived cell lines. Therio. 34:865–877.

Polge, C., Embryo transplantation and preservation, In: Cole, D. J. A., Foxcroft, GTR. (eds), Control of Pig Reproduction, London; Butterworth Scientific; 1982:277–291.

Rexroad, C. E. and Pursel, V. G. 1988. Status of gene transfer in domestic animals. 11th International Congress on Animal Reprod. & Artificial Insemination 5:29.

Robertson, E. J., 1987, Embryo-derived stem cell lines, in Teratocarcinomas and embryonic stem cells: a practical approach, Robertson (ed.), pp. 71–112. IRL Press, Ltd., Oxford, England.

Robertson, E. J. 1987. Pluripotential stem cell lines as a route into the mouse germ line. Trends Genet. 2:9–13.

Rudnicki, M. A. and McBurney, M. W., Cell culture methods and induction of differentiation of approach, (E. J. Robertson, Ed.), pp. 19–49. IRL Press Limited, Oxford, England.

Smith, A. G. and M. L. Hooper. 1987, Buffalo rat liver cells produce a diffusible activity which inhibits the differentiation of murine embryonal carcinomas and embryonic stem cells. Dev. Biol. 121:1.

Strojek, R. M. et al., 1990, A method for cultivating morphologically undifferented embryonic stem cells from porcine blastocysts, Herrogenology 33:901–913.

Thomas, K. R., Capecchi, M. R. 1987. Site-directed mutagenesis by gene targeting in mouse embryo-derived stem cells. Cell 51:503–512.

Wall, R. J., Pursel, V. G., Shamay, A., McKnight, R. A., Pittius, C. W., and Henninhausen, L. (1991) High level synthesis of a heterologous milk protein in the mammary glands of transgenic swine. Proc. Natl. Acad. Scie. USA 88, 1696–1700.

Webel, S. K., Peters, J. B., Anderson, L. L., Synchronous and asynchronous transfer of embryos in the pig. J. Animal Science 1970; 30:565–568.

What is claimed is:

1. A method of obtaining an embryonic stem cell for incorporation into a swine embryo to form a chimeric swine, said method comprising:

(a) introducing a cell from a culture made by:

(i) culturing dissociated cells from a swine embryo in conditioned stem cell medium in the presence or absence of a feeder layer, and (ii) subculturing the culture until a stable culture with morphological features and growth parameters characteristic of an embryonic stem cell culture is established, into a SCID mouse;

(b) allowing a tumor to form in the mouse from the cell; and (c) obtaining an embryonic stem cell from a culture that is shown to be capable of producing a tumor in step b.

2. The method of claim 1, wherein the embryonic stem cell is characterized by an undifferentiated morphology indistinguishable from the morphology of a cell from the culture of step a of claim 1 from which a cell formed a tumor in step b of claim 1.

3. A method for determining the cell types in which a genetic complement is expressed, said method comprising:

(a) introducing a swine embryonic stem cell Which comprises the genetic complement into an immunocompromised mouse to produce a tumor;

(b) placing the tumor in suitable conditions to allow the tumor to differentiate into a plurality of recognizable cell types and to empress the genetic complement;

(c) excising the tumor; and (d) analyzing the differentiated cell types to determine in which cell types the genetic complement is expressed.

4. An embryonic stem cell obtained from a culture that is capable of forming a tumor in a SCIDS mouse in accordance with the method of claim 1.

5. A culture initiated from an embryonic stem cell of claim 4.

* * * * *

UNITED STATES PATENT AND TRADEMARK OFFICE
CERTIFICATE OF CORRECTION

PATENT NO. : 5,523,226
DATED : June 4, 1996
INVENTOR(S) : Matthew B. Wheeler

It is certified that error appears in the above-indentified patent and that said Letters Patent is hereby corrected as shown below:

On the Title Page

Item [56]: under the heading "OTHER PUBLICATIONS", line 7, delete "Embryyo" and substitute --Embryo--.

On page 2, under the heading "OTHER PUBLICATIONS", column 2, line 3, delete "Kolias" and substitute --Kollias--.

On page 2, under the heading "OTHER PUBLICATIONS", column 2, line 4, before "Academic", insert --eds,--.

In the Claims

In Claim 3, column 30, line 3, delete "Which" and substitute --which--.

In Claim 3, column 30, line 8, delete "empress" and substitute --express--.

Signed and Sealed this

Thirtieth Day of December, 1997

Attest:

BRUCE LEHMAN

*Attesting Officer*  *Commissioner of Patents and Trademarks*